(12) United States Patent
De Luca et al.

(10) Patent No.: US 7,713,947 B2
(45) Date of Patent: May 11, 2010

(54) CLADRIBINE REGIMEN FOR TREATING MULTIPLE SCLEROSIS

(75) Inventors: Giampiero De Luca, Conches/Geneva (CH); Arnaud Ythier, Collex-Bossy (CH); Alain Munafo, Tartegnin (CH); Maria Lopez-Bresnahan, Lincoln, MA (US)

(73) Assignee: Merck Serono S.A., Coinsins, Vaud (CH)

( * ) Notice: Subject to any disclaimer, the term of this patent is extended or adjusted under 35 U.S.C. 154(b) by 300 days.

(21) Appl. No.: 11/722,018

(22) PCT Filed: Dec. 20, 2005

(86) PCT No.: PCT/EP2005/056954

§ 371 (c)(1),
(2), (4) Date: Jun. 18, 2007

(87) PCT Pub. No.: WO2006/067141

PCT Pub. Date: Jun. 29, 2006

(65) Prior Publication Data

US 2009/0081163 A1    Mar. 26, 2009

Related U.S. Application Data

(60) Provisional application No. 60/638,669, filed on Dec. 22, 2004.

(30) Foreign Application Priority Data

Dec. 22, 2004   (EP)   ................... 04106909

(51) Int. Cl.
  *A61K 31/52*   (2006.01)
  *A61K 31/7076*  (2006.01)
  *A61K 38/21*   (2006.01)
  *A61K 9/00*    (2006.01)

(52) U.S. Cl. ...................... 514/46; 424/85.6

(58) Field of Classification Search ............ None
See application file for complete search history.

(56) References Cited

U.S. PATENT DOCUMENTS 4,964,848 A * 10/1990 Bloom ............... 604/6.03
5,506,214 A *  4/1996 Beutler ............... 514/46

2010/0021429 A1 * 1/2010 Brentzel et al. ........ 424/85.6

FOREIGN PATENT DOCUMENTS

EP        0 626 853 B1   4/2000
WO    WO 2004/087101 A2  10/2004

OTHER PUBLICATIONS

Beutler, E. et al. "Marrow Suppression Produced by Repeated Doses of Cladribine", *Acta Haematol*, 1994, pp. 10-15, vol. 91.
Beutler, E. et al. "Treatment of Multiple Sclerosis and Other Autoimmune Diseases With Cladribine", *Seminars in Hematology*, Jan. 1, 1996, pp. 45-52, vol. 33, No. 1, Supplement 1.
Beutler, E. et al. "The treatment of chronic progressive multiple sclerosis with cladribine", *Proc. Natl. Acad. Sci. USA*, Feb. 1996, pp. 1716-1720, vol. 93.
Ellison, G. et al. "Oral Cladribine for Multiple Sclerosis", *Neurology*, Mar. 1997, P03.070, pp. A174-A175, vol. 48, No. 3, XP008047069.
Grieb, P. et al. "Effect of Repeated Treatments with Cladribine (2-Chlorodeoxyadenosine) on Blood Counts in Multiple Sclerosis Patients", *Archivum Immunologiae et Therapiae Experimentalis*, 1995, pp. 323-327, vol. 43, No. 5-6.
Kazimierczuk, Z. et al. "Synthesis of 2'-Deoxytubercidin, 2'-Deoxyadenosine, and Related 2'-Deoxynucleosides via a Novel Direct Stereospecific Sodium Salt Glycosylation Procedure", *J. Am. Chem. Soc.*, 1984, pp. 6379-6382, vol. 106, No. 21.
Kurtzke, J. "Rating neurologic impairment in multiple sclerosis: An expanded disability status scale (EDSS)", *Neurology*, Nov. 1983, pp. 1444-1452, vol. 33.
Langtry, H. et al. "Cladribine: A Review of its Use in Multiple Sclerosis", *Biodrugs*, May 1998, pp. 419-433, vol. 9, No. 3.
Lassmann, H. et al. "Heterogeneity of multiple sclerosis pathogenesis: implications for diagnosis and therapy", *TRENDS in Molecular Medicine*, Mar. 2001, pp. 115-121, vol. 7, No. 3.
Lublin, F. et al. "Defining the clinical course of multiple sclerosis: Results of an international survey", *Neurology*, Apr. 1996, pp. 907-911, vol. 46.
Lucchinetti, C. et al. "Multiple sclerosis: recent developments in neuropathology, pathogenesis, magnetic resonance imaging studies and treatment", *Current Opinion in Neurology*, 2001, pp. 259-269, vol. 14.

(Continued)

*Primary Examiner*—Elizabeth C. Kemmerer
*Assistant Examiner*—Kimberly A. Ballard
(74) *Attorney, Agent, or Firm*—Saliwanchik, Lloyd & Saliwanchik

(57) ABSTRACT

The present invention is related to the use of Cladribine for the preparation of a pharmaceutical formulation for the treatment of multiple sclerosis, especially relapsing-remitting multiple sclerosis or early secondary progressive multiple sclerosis, wherein the preparation is to be orally administered and wherein re-treatments are possible.

48 Claims, No Drawings

OTHER PUBLICATIONS

Mattson, D. "Update on the diagnosis of multiple sclerosis", *Expert Review of Neurotherapeutics*, May 2002, pp. 319-327, vol. 2, No. 3.

McDonald, W. et al. "Recommended Diagnostic Criteria for Multiple Sclerosis: Guidlines from the International Panel on the Diagnosis of Multiple Sclerosis", *Annals of Neurology*, Jul. 2001, pp. 121-127, vol. 50, No. 1.

Miller, R. et al. "Therapeutic advances in ALS", *Neurology*, 1996, pp. S217, vol. 47, Suppl. 4.

Noseworthy, J. et al. "Multiple Sclerosis", *The New England Journal of Medicine*, Sep. 28, 2000, pp. 938-952, vol. 343, No. 13.

Poser, C. et al. "New Diagnostic Criteria for Multiple Sclerosis: Guidelines for Research Protocols", *Annals of Neurology*, Mar. 1983, pp. 227-231, vol. 13, No. 3.

Rice, G. et al. "Cladribine and progressive MS: Clinical and MRI outcomes of a multicenter controlled trial", *Neurology*, Mar. 2000, pp. 1145-1155, vol. 54.

Romine, J. et al. "A Double-Blind, Placebo-Controlled, Randomized Trial of Cladribine in Relapsing-Remitting Multiple Sclerosis", *Proceedings of the Association of American Physicians*, Jan./Feb. 1999, pp. 35-44, vol. 111, No. 1.

Schumacher, G. et al. "Problems of Experimental Trials of Therapy in Multiple Sclerosis: Report by the Panel on the Evaluation of Experimental Trials of Therapy in Multiple Sclerosis", *Annals New York Academy of Sciences*, Mar. 31, 1965, pp. 552-568, vol. 122.

Selby, R. et al. "Safety and Tolerability of Subcutaneous Cladribine Therapy in Progressive Multiple Sclerosis", *Can. J. Neurol. Sci.*, 1998, pp. 295-299, vol. 25.

Sipe, J. et al. "A neurologic rating scale (NRS) for use in multiple sclerosis", *Neurology*, Oct. 1984, pp. 1368-1372, vol. 34.

Stelmasiak, Z. et al. "A pilot trial of cladribine (2-chlorodeoxyadenosine) in remitting-relapsing multiple sclerosis", *Med. Sci Monit.*, 1998, pp. 4-8, vol. 4, No. 1.

\* cited by examiner

CLADRIBINE REGIMEN FOR TREATING MULTIPLE SCLEROSIS

CROSS-REFERENCE TO RELATED APPLICATION

This application is the U.S. national stage application of International Patent Application No. PCT/EP2005/056954, filed Dec. 20, 2005, which claims the benefit of U.S. Provisional Patent Application No. 60/638,669, filed Dec. 22, 2004, the disclosures of which are hereby incorporated by reference in their entireties, including all figures, tables and amino acid or nucleic acid sequences.

FIELD OF THE INVENTION

The present invention relates to the use of multiple doses of Cladribine for the treatment of multiple sclerosis, especially relapsing-remitting multiple sclerosis or early secondary progressive multiple sclerosis.

BACKGROUND OF THE INVENTION

Multiple sclerosis (MS) is the most known chronic inflammatory demyelinating disease of the central nervous system in humans. The onset of the disease typically occurs during ages 20 to 40. Women are affected approximately twice as often as men.

Over time, MS may result in the accumulation of various neurological disabilities. Clinical is disability in MS is presumed to be a result of repeated inflammatory injury with subsequent loss of myelin and axons, leading to tissue atrophy.

MS is manifested in physical symptoms (relapses and disability progression), Central Nervous System (CNS) inflammation, brain atrophy and cognitive impairment. Presenting symptoms include focal sensory deficits, focal weakness, visual problems, imbalance and fatigue. Sexual impairment and sphincter dysfunction may occur. Approximately half of the patients with MS may experience cognitive impairment or depression.

MS is now considered to be a multi-phasic disease and periods of clinical quiescence (remissions) occur between exacerbations. Remissions vary in length and may last several years but are infrequently permanent.

Four courses of the disease are individualized: relapsing-remitting (RR), secondary progressive (SP), primary progressive (PP) and progressive relapsing (PR) multiple sclerosis.

More than 80% of patients with MS will initially display a RR course with clinical exacerbation of neurological symptoms, followed by a recovery that may or may not be complete (Lublin and Reingold, *Neurology*, 1996, 46:907-911).

During RRMS, accumulation of disability results from incomplete recovery from relapses. Approximately, half of the patients with RRMS switch to a progressive course, called SPMS, 10 years after the diseased onset. During the SP phase, worsening of disability results from the accumulation of residual symptoms after exarcerbation but also from insidious progression between exacerbations (Lublin and Reingold above). 10% of MS patients have PPMS which is characterized by insidious progression of the symptoms from the disease onset. Less than 5% of patients have PRMS and are often considered to have the same prognosis as PPMS. It is suggested that distinct pathogenic mechanisms may be involved in different patient sub-groups and have wide-ranging implications for disease classification (Lassmann et al., 2001, *Trends Mol. Med.*, 7, 115-121; Lucchinetti et al., *Curr. Opin. Neurol.*, 2001, 14, 259-269).

MS onset is defined by the occurrence of the first neurological symptoms of CNS dysfunction. Advances in cerebrospinal fluid (CSF) analysis and magnetic resonance imaging (MRI) have simplified the diagnostic process and facilitated early diagnostic (Noseworthy et al., *The New England Journal of Medicine*, 2000, 343, 13, 938-952). The International Panel on the Diagnosis of MS issued revised criteria facilitating the diagnosis of MS and including MRI together with clinical and para-clinical diagnostic methods (Mc Donald et al., 2001, *Ann. Neurol.*, 50:121-127).

Current medications for MS which are disease modifying treatments, i.e. modifying the course of MS, modulate or suppress the immune system. There are four FDA approved immunomodulating agents for RRMS: three beta interferons (Betaseron®, Berlex; Avonex®, Biogen; Rebif®, Serono) and Glatimarer Acetate (Copaxone®, Amgen). There is also one FDA approved immunosuppressing drug for worsening MS, Mitoxantrone (Novantrone®, Amgen). Several other immunosuppressive agents are used, although not FDA approved.

Among them, Cladribine, a chlorinated purine analogue 2-chloro-2'deoxyadenosine analogue (2-CdA), has been suggested to be useful in the treatment of MS (EP 626853B1 and U.S. Pat. No. 5,506,214).

Several clinical studies with Cladribine in patients with multiple sclerosis have investigated the use of i.v. and s.c. Cladribine in MS.

Two double-blind, placebo controlled Phase II studies were conducted respectively in the treatment of Chronic Progressive MS (Selby et al., 1998, *Can. J. Neurol. Sci.*, 25:295-299) and Relapsing-Remitting MS respectively (Romine et al., 1999, *Proceedings of the Association of American Physicians*, 111, 1, 35-44).

In the first trial, the Cladribine dose used was 0.1 mg/kg/day for 7 days by continuous i.v. infusion. The treatment for repeated for 4 consecutive months.

In the second clinical trial, the Cladribine dose used was 0.07 mg/kg/day for 5 days by subcutaneous injection. The treatment was repeated for 6 consecutive months.

In addition, placebo controlled Phase III study was conducted in patients with primary progressive (PP) or secondary progressive (SP) multiple sclerosis (Rice at al., 2000, *Neurology*, 54, 5, 1145-1155). In this study, both patient groups received Cladribine by subcutaneous injection at a dose of 0.07 mg/kg/day. The treatment was repeated for either 2 months or 6 months.

The Phase II clinical studies provided evidence for the positive effects of Cladribine in patients with MS in terms of Kutzke Extended Disability Status Scale (EDSS), Scripps Neurologic rating Scale (SNRS) scores and Magnetic Resonance Imaging (MRI) findings (Beutler et al., 1996, *Proc. Nat. Acad. Sci. USA*, 93, 1716-1720; Romine et al., 1999 above). Phase II study results, were positive on the significant reduction of MRI-measured brain lesions (Rice at al., 2000, above).

Some adverse effects (AEs), such as increased incidence of infections related to compromised immune function or myelosuppression, were observed with the highest doses (Selby et al., 1998, above; Beutler et al., 1994, *Acta hematol*, 91:10-15). Due to the narrow margin of safety between the efficacy dose and the dose of occurrence of AEs, to date, all clinical trials for Cladribine in multiple sclerosis have been conducted using either i.v. or s.c. administration. As a result, Beutler et al. (Beutler et al., 1996, *Seminars in Hematology*, 33, 1(S1), 45-52) excluded the oral route for the treatment of multiple sclerosis with Cladribine.

Grieb et al. reported a small trial in 11 patients with remitting-relapsing multiple sclerosis (Grieb et al., 1995, *Archivum Immunologiae et Therapiae Experimentalis*, 43 (5-6), 323-327) wherein Cladribine has been orally administered during 6 monthly courses of 5 days at a total dose of about 4-5.7 mg/kg (patients of about 52 and about 75 kilos, respectively) i.e. a total effective dose of 2-2.85 mg/kg. For some patients, a single re-treatment of 5 days was performed at a cumulative dose of 0.4-0.66 mg/kg after a cladribine free-period of 3 or 6 months. The side effects observed with the regimen above were said to be less severe than the ones observed in the study on patients suffering from chronic progressive multiple sclerosis treated by i.v. infusion of Cladribine (Sipe et al., 1994, *Lancet*, 344, 9-13) but were still present. In addition, the therapeutic efficacy of the oral regimen above versus the i.v. infusion therapy was questioned (Grieb et al., 1995, above) and a group of "non-responders" has been identified (Stelmasiak et al., 1998, *Laboratory Investigations*, 4(1), 4-8).

Therefore, it would be desirable to have a method for treating multiple sclerosis comprising the oral administration of Cladribine that would permit the same or improved effect on MS lesions while decreasing the occurrence and/or severity adverse events. In addition, as MS is a chronic disease, it would be desirable to decrease the occurrence and/or severity adverse events in such a way that re-treatments are possible. A sustained benefit of Cladribine treatment between the treatment periods is also desirable.

SUMMARY OF THE INVENTION

The present invention is directed towards a use of Cladribine for the preparation of a pharmaceutical formulation for the treatment of multiple sclerosis, wherein the preparation is to be the orally administered. Particularly, the invention is directed towards a use of Cladribine for the preparation of a medicament for the treatment of relapsing-remitting multiple sclerosis or early secondary progressive multiple sclerosis and wherein re-treatments are possible.

An embodiment of the invention provides an improved dosing regimen for Cladribine in the treatment of multiple sclerosis.

An additional embodiment of the invention provides a use of Cladribine for the preparation of a pharmaceutical formulation for the treatment of multiple sclerosis wherein adverse effects are reduced, allowing further use of Cladribine.

In one embodiment, the invention provides a use of Cladribine for the preparation of a pharmaceutical formulation wherein the formulation is to be orally administered following the sequential steps below:
  (i) An induction period wherein the Cladribine pharmaceutical formulation is administered and wherein the total dose of Cladribine reached at the end of the induction period is from about 1.7 mg/kg to about 3.5 mg/kg;
  (ii) A Cladribine-free period wherein no Cladribine is administered;
  (iii) A maintenance period wherein Cladribine pharmaceutical formulation is administered and wherein the total dose of Cladribine reached at the end of the maintenance period is lower than the total dose of Cladribine reached at the end of the induction period (i);
  (iv) A Cladribine-free period wherein no Cladribine is administered.

In another embodiment, the invention provides a method for the treatment of multiple sclerosis, comprising the oral administration of Cladribine or of a formulation thereof in a patient in need thereof comprising the following steps:
  (i) An induction treatment wherein the total dose of Cladribine reached at the end of the induction period is from about 1.7 mg/kg to about 3.5 mg/kg;
  (ii) A Cladribine-free period wherein no Cladribine is administered;
  (iii) A maintenance treatment wherein the total dose of Cladribine reached at the end of the maintenance period is lower than the total dose of Cladribine reached at the end of the induction period (i);
  (iv) A Cladribine-free period wherein no Cladribine is administered.

DETAILED DESCRIPTION OF THE INVENTION

Definitions

The "total dose" or "cumulative dose" refers to the total dose of Cladribine administered during the treatment, i.e. the dose reached at the end of the treatment that is calculated by adding the daily doses. For example, the total dose of Cladribine corresponding to a treatment of 0.7 mg/kg Cladribine per day during 5 days is 3.5 mg/kg or the total dose of Cladribine corresponding to a treatment of 0.35 mg/kg Cladribine per day during 5 days is 1.7 mg/kg.

"The total effective dose" or "cumulative effective dose" refers to the bioavailable dose of Cladribine after a given administration period, i.e. the bioavailable dose reached at the end of the treatment that is calculated by adding the daily doses reduced by the bioavailability coefficient. For example, the total effective dose of Cladribine corresponding to a treatment of 0.7 mg/kg Cladribine per day during 5 days wherein the bioavailability of Cladribine is of about 40% is 1.4 mg/kg or the total effective dose of Cladribine corresponding to a treatment of 0.35 mg/kg Cladribine per day during 5 days wherein the bioavailability of Cladribine is of about 40% is 0.7 mg/kg.

Typically, the bioavailability of Cladribine or of a Cladribine formulation used in the context of this invention is from about 30% to about 90%, preferably from about 40% to about 60%, such as about 50%.

"A week" refers to a period of time of or about 5, about 6 or about 7 days.

"A month" refers to a period of time of or about 28, about 29, about 30 or about 31 days.

"Treatment" comprises the sequential succession of an "induction treatment" and at least a "maintenance treatment". Typically, a treatment according to the invention comprises an "induction treatment" and about one or about two or about three maintenance treatments. Typically, a treatment according to the invention is of about 2 years (about 24 months) or about 3 years (about 36 months) or about 4 years (about 48 months).

An "Induction Treatment" consists in the sequential succession of (i) an induction period wherein the Cladribine or the Cladribine pharmaceutical preparation of the invention is orally administered and (ii) a Cladribine-free period. An induction period lasts up to about 4 months or up to about 3 month or up to about 2 months. For example, an induction period lasts for about 2 to about 4 months. An induction period consists in the oral administration of Cladribine or a pharmaceutical preparation thereof during about 1 to about 7 days each month.

A "Cladribine-free period" is a period wherein no Cladribine is administered to the patient. During a Cladribine-free period, the patient can be free of any administration or be dosed with a placebo-pill or another drug except. A Cladribine-free period lasts up to about 10 months or up to 9 months or up to about 8 months. For example, a Cladribine-free period lasts from about 8 to about 10 months, typically at least of about 8 months.

A "Maintenance Treatment" consists in the sequential succession of (i) a maintenance period wherein the Cladribine or the Cladribine pharmaceutical preparation of the invention is orally administered at a lower dose than the Cladribine dose orally administered during the induction treatment and (ii) a Cladribine-free period. A maintenance period lasts for up to about 4 months, or up to about 3 months, or up to about 2 months, preferably up to about 2 months. For example, a maintenance period lasts for about 2 to about 4 months, preferably for about 2 months. A maintenance period consists in the oral administration of Cladribine or of a pharmaceutical preparation thereof during about 1 to about 7 days each month.

Within the context of this invention, the beneficial effect, including but not limited to an attenuation, reduction, decrease or diminishing of the pathological development after onset of the disease, may be seen after one or more a "treatments", after an "induction treatment", after a "maintenance treatment" or during a Cladribine-free period.

"Daily dose" refers to the total dose of Cladribine orally administered to the patient each day of administration. The daily dose can be reached through a single or several administrations per day, such as for example once a day, twice a day or three times a day.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Patients suffering from MS can be defined for example as having clinically definite or laboratory-definite MS according to Schumacher or Poser criteria (Schumacher et al., 1965, Ann. NY Acad. Sci. 1965; 122:552-568; Poser et al., 1983, Ann. Neurol. 13(3): 227-31).

"Relapses" involve neurologic problems that occur over a short period, typically days but sometimes as short as hours or even minutes. These attacks most often involve motor, sensory, visual or coordination problems early in the disease. Later, bladder, bowel, sexual and cognitive problems may be shown. Sometimes the attack onset occurs over several weeks. Typical MS relapse involves a period of worsening, with development of neurological deficits, then a plateau, in which the patient is not getting any better but also not getting any worse followed by a recovery period. Recovery usually begins within a few weeks.

"Efficacy" of a treatment according to the invention can be measured based on changes in the course of disease in response to a use according to the invention. For example, treatment of MS efficacy can be measured by the frequency of relapses in RRMS and the presence or absence of new lesions in the CNS as detected using methods such as MRI technique (Miller et al., 1996, Neurology, 47(Suppl 4): S217; Evans et al., 1997, Ann. Neurology, 41:125-132).

The observation of the reduction and/or suppression of MRI $T_1$ gadolinium-enhanced lesions (thought to represent areas of active inflammation) gives a primary efficacy variable.

Secondary efficacy variables include MRI $T_1$ enhanced brain lesion volume, MRI $T_1$ enhanced lesion number, MRI $T_2$ lesion volume (thought to represent total disease burden, i.e. demyelination, gliosis, inflammation and axon loss), MRI $T_1$ enhanced hypointense lesion volume (thought to represent primarily demyelination and axon loss), time-to-progression of MS, frequency and severity of exacerbations and time-to-exacerbation, Expanded Disability Status Scale score and Scripps Neurologic Rating Scale (SNRS) score (Sipe et al., 1984, Neurology, 34, 1368-1372). Methods of early and accurate diagnosis of multiple sclerosis and of following the disease progression are described in Mattson, 2002, Expert Rev. Neurotherapeutics, 319-328.

Degree of disability of MS patients can be for example measured by Kurtzke Expanded Disability Status Scale (EDSS) score (Kurtzke, 1983, Neurology, 33, 1444-1452). Typically a decrease in EDSS score corresponds to an improvement in the disease and conversely, an increase in EDSS score corresponds to a worsening of the disease.

Cladribine (2-CdA)

2-CdA and its pharmacologically acceptable salts may be used in the practice of this invention.

Cladribine can be formulated in any pharmaceutical preparation suitable for oral administration. Representative oral formulations of 2-CdA are described in (WO 96/19230; WO 96/19229; U.S. Pat. Nos. 6,194,395; 5,506,214; WO 2004/087100; WO 2004/087101), the contents of which are incorporated herein by reference. Examples of ingredients for oral formulations are given below.

Processes for preparing 2-CdA are well known in the art. For example, the preparation of 2-CdA is described in (EP 173,059; WO 04/028462; WO 04/028462; U.S. Pat. No. 5,208,327; WO 00/64918) and Robins et al., J. Am. Chem. Soc., 1984, 106: 6379. Alternatively, pharmaceutical preparations of 2-CdA may be purchased from Bedford Laboratories, Bedford, Ohio.

Oral administration of Cladribine may be in capsule, tablet, oral suspension, or syrup form. The tablet or capsules may contain from about 3 to 500 mg of Cladribine. Preferably they may contain about 3 to about 10 mg of Cladribine, more preferably about 3, about 5 or about 10 mg of Cladribine. The capsules may be gelatin capsules and may contain, in addition to Cladribine in the quantity indicated above, a small quantity, for example less than 5% by weight, magnesium stearate or other excipient. Tablets may contain the foregoing amount of the compound and a binder, which may be a gelatin solution, a starch paste in water, polyvinyl alcohol in water, etc. with a typical sugar coating.

Compositions

Compositions of this invention may further comprise one or more pharmaceutically acceptable additional ingredient(s) such as alum, stabilizers, antimicrobial agents, buffers, coloring agents, flavoring agents, adjuvants, and the like.

Compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

Compositions of this invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, non-aqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Combination

According to the invention, Cladribine can be administered alone or in combination with IFN-beta, prophylactically or therapeutically to an individual prior to, simultaneously or sequentially with other therapeutic regimens or agents (e.g. multiple drug regimens), in a therapeutically effective amount, especially therapeutic agents for the treatment of multiple sclerosis. Active agents that are administered simultaneously with other therapeutic agents can be administered in the same or different compositions and in the same or different routes of administration.

In one embodiment, when Cladribine is administered in combination with WFN-beta, WFN-beta is administered during the Cladribine-free period.

In another embodiment, when Cladribine is administered in combination with IFN-beta, IFN-beta is administered after the "treatment" according to the invention.

The term "interferon-beta (IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments.

IFN-β suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogs and active fragments thereof.

Rebif® (recombinant human interferon-β) is the latest development in interferon therapy for multiple sclerosis (MS) and represents a significant advance in treatment. Rebi® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

The dosing of IFN-β in the treatment of relapsing-remitting MS according to the invention depends on the type of IFN-β used.

In accordance with the present invention, where IFN is recombinant IFN-β1b produced in *E. Coli*, commercially available under the trademark Betaseron®, it may preferably be administered sub-cutaneously every second day at a dosage of about of 250 to 300 µg or 8 MIU to 9.6 MIU per person.

In accordance with the present invention, where IFN is recombinant IFN-β1a, produced in Chinese Hamster Ovary cells (CHO cells), commercially available under the trademark Avonex®, it may preferably be administered intramuscularly once a week at a dosage of about of 30 µg to 33 µg or 6 MIU to 6.6 MIU per person.

In accordance with the present invention, when IFN is recombinant IFN-β1a, produced in Chinese Hamster Ovary cells (CHO cells), commercially available under the trademark Rebif®, it may preferably be administered sub-cutaneously three times a week (TIW) at a dosage of 22 to 44 µg or 6 MIU to 12 MIU per person.

Patients

Patients according to the invention are patients suffering from multiple sclerosis, preferably RRMS or early SPMS.

In an embodiment of the invention, patients are selected from human males or females between 18 and 55 years age.

In another embodiment of the invention, patients had at least one relapse within the prior 12 months of the treatment.

Use According to the Invention

In one embodiment, the invention provides a use of Cladribine for the preparation of a pharmaceutical formulation for the treatment of multiple sclerosis wherein the formulation is to be orally administered following the sequential steps below:
   (i) An induction period wherein Cladribine pharmaceutical formulation is administered and wherein the total dose of Cladribine reached at the end of the induction period is from about 1.7 mg/kg to about 3.5 mg/kg;
   (ii) A Cladribine-free period wherein no Cladribine is administered;
   (iii) A maintenance period wherein Cladribine pharmaceutical formulation is administered and wherein the total dose of Cladribine reached at the end of the maintenance period is lower than the total dose of Cladribine reached at the end of the induction period (i);
   (iv) A Cladribine-free period wherein no Cladribine is administered.

In a further embodiment, the invention provides a use according to the invention wherein the induction period lasts up to about 4 months or up to about 3 months or up to about 2 months.

In a further embodiment, the invention provides a use according to the invention wherein the induction period lasts up to about 2 months.

In a further embodiment, the invention provides a use according to the invention wherein the induction period lasts up to about 4 months.

In a further embodiment, the invention provides a use according to the invention wherein the total dose of Cladribine reached at the end of the induction period is about 1.7 mg/kg.

In a further embodiment, the invention provides a use according to the invention wherein the total dose of Cladribine reached at the end of the induction period is about 3.5 mg/kg.

In another further embodiment, the invention provides a use according to the invention wherein the Cladribine-free period lasts up to about 10 months, or up to about 9 months or up to about 8 months.

In another further embodiment, the invention provides a use according to the invention wherein the Cladribine-free (ii) period lasts up to about 8 months.

In another further embodiment, the invention provides a use according to the invention wherein the Cladribine-free (ii) period lasts at least about 8 months.

In another further embodiment, the invention provides a use according to the invention wherein the Cladribine-free period (ii) lasts up to about 10 months.

In another further embodiment, the invention provides a use according to the invention wherein the Cladribine-free (iv) period lasts up to about 10 months.

In another further embodiment, the invention provides a use according to the invention wherein the Cladribine-free (iv) period lasts at least about 8 months.

In another further embodiment, the invention provides a use according to the invention wherein the Cladribine-free periods (ii) and/or (iv) last between about 8 and about 10 months.

In another further embodiment, the invention provides a use according to the invention wherein a placebo-pill is administered during the Cladribine-free period.

In another further embodiment, the invention provides a use according to the invention wherein the Cladribine-free period is free of any administration.

In another further embodiment, the invention provides a use according to the invention wherein the maintenance period lasts up to about 4 months, or up to about 3 months, or up to about 2 months, preferably up to about 2 months.

In another further embodiment, the invention provides a use according to the invention wherein the total dose of Cladribine reached at the end of the maintenance period (iii) is about 1.7 mg/kg.

In another further embodiment, the invention provides a use according to the invention wherein the steps (iii) to (iv) are repeated at least one or two times.

In a preferred embodiment, the invention provides a use of Cladribine for the preparation of a pharmaceutical formulation for the treatment of multiple sclerosis wherein the formulation is to be orally administered following the sequential steps below:
  (i) An induction period wherein Cladribine pharmaceutical formulation is administered and wherein the total dose of Cladribine reached at the end of the induction period is from about 1.7 mg/kg to about 3.5 mg/kg;
  (ii) A Cladribine-free period wherein no Cladribine is administered;
  (iii) A maintenance period wherein Cladribine pharmaceutical formulation is administered and wherein the total dose of Cladribine reached at the end of the maintenance period is lower than the total dose of Cladribine reached at the end of the induction period (i)
  (iv) A Cladribine-free period wherein no Cladribine is administered;

wherein the induction period last up to about 4 months, or up to about 3 months, or up to about 2 months; the Cladribine-free period (ii) lasts up to about 10 months, or up to about 9 months, or up to about 8 months; the maintenance period (iii) lasts up to about 2 months; the Cladribine-free period (iv) lasts up to about 10 months; the total dose of Cladribine reached at the end of the maintenance period is about 1.7 mg/kg and steps (iii) to (iv) are repeated performed one, two or three times.

In another embodiment, the invention provides a use of Cladribine for the preparation of a pharmaceutical formulation for the treatment of multiple sclerosis wherein the formulation is to be orally administered following the sequential steps below:
  (i) An induction period wherein Cladribine pharmaceutical formulation is administered and wherein the total effective dose of Cladribine reached at the end of the induction period is from about 0.7 mg/kg to about 1.4 mg/kg;
  (ii) A Cladribine-free period wherein no Cladribine is administered;
  (iii) A maintenance period wherein Cladribine pharmaceutical formulation is administered and wherein the total effective dose of Cladribine reached at the end of the maintenance period (iii) is lower than the total effective dose of Cladribine reached at the end of the induction period (i);
  (iv) A Cladribine-free period wherein no Cladribine is administered.

In a further embodiment, the invention provides a use of Cladribine for the preparation of a pharmaceutical formulation for the treatment of multiple sclerosis wherein the formulation is to be orally administered following the sequential steps below:
  (i) An induction period wherein Cladribine pharmaceutical formulation is administered and wherein the total effective dose of Cladribine reached at the end of the induction period is from about 0.7 mg/kg to about 1.4 mg/kg;
  (ii) A Cladribine-free period wherein no Cladribine is administered;
  (iii) A maintenance period wherein Cladribine pharmaceutical formulation is administered and wherein the total effective dose of Cladribine reached at the end of the maintenance period is lower than the total effective dose of Cladribine reached at the end of the induction period (i);
  (iv) A Cladribine-free period wherein no Cladribine is administered;

wherein the induction period lasts up to about 4 months, or up to about 3 months, or up to about 2 months; the Cladribine-free period (ii) lasts up to about 10 months, or up to about 9 months, or up to about 8 months; the maintenance period (iii) lasts up to about 2 months; the Cladribine-free period (ii) lasts up to about 10 months; the total effective dose of Cladribine reached at the end of the maintenance period is about 0.7 mg/kg and steps (iii) to (iv) are repeated performed one, two or three times.

In a preferred embodiment, the invention provides Cladribine for use as a medicament for the treatment of multiple sclerosis wherein the medicament is to be orally administered following the sequential steps below:
  (i) An induction period wherein Cladribine pharmaceutical formulation is administered and wherein the total dose of Cladribine reached at the end of the induction period is from about 1.7 mg/kg to about 3.5 mg/kg;
  (ii) A Cladribine-free period wherein no Cladribine is administered;
  (iii) A maintenance period wherein Cladribine pharmaceutical formulation is administered and wherein the total dose of Cladribine reached at the end of the maintenance period is lower than the total dose of Cladribine reached at the end of the induction period (i);
  (iv) A Cladribine-free period wherein no Cladribine is administered;

wherein the induction period last up to about 4 months, or up to about 3 months, or up to about 2 months; the Cladribine-free period (ii) lasts up to about 10 months, or up to about 9 months, or up to about 8 months; the maintenance period (iii) lasts up to about 2 months; the Cladribine-free period (iv) lasts up to about 10 months; the total dose of Cladribine reached at the end of the maintenance period is about 1.7 mg/kg and steps (iii) to (iv) are repeated performed one, two or three times.

In another embodiment, the invention provides a use of Cladribine according to the invention wherein the pharmaceutical formulation is to be orally administered at a daily dose of Cladribine about 3 to 30 mg Cladribine, preferably 5 to 20 mg Cladribine, most preferably 10 mg Cladribine.

In another further embodiment, the invention provides a use according to the invention wherein the total dose of Cladribine reached at the end of the induction period is about 3.5 mg/kg and the total dose of Cladribine reached at the end of the maintenance period is about 1.7 mg/kg.

In another further embodiment, the invention provides a use according to the invention wherein the total effective dose of Cladribine reached at the end of the induction period is about 1.4 mg/kg and the total effective dose of Cladribine reached at the end of the maintenance period is about 0.7 mg/kg.

In another embodiment, the invention provides a use of Cladribine according to the invention wherein the pharmaceutical formulation is to be orally administered once a day during the induction period.

In another embodiment, the invention provides a use of Cladribine according to the invention wherein the pharmaceutical formulation is to be orally administered several times a day administered once a day during the induction period, preferably twice or three times a day, more preferably twice a day.

In another embodiment, the invention provides a use of Cladribine according to the invention whereby the pharmaceutical formulation is orally administered about 1 to about 7 days per month, preferably from about 5 to about 7 days per month during the induction period.

In another embodiment, the invention provides a use of Cladribine according to the invention whereby the pharmaceutical formulation is orally administered about 0.02 days/ kg to about 0.08 days/kg per month during the induction period.

In another embodiment, the invention provides a use of Cladribine according to the invention whereby the pharmaceutical formulation is orally administered about 0.02 days/ kg to about 0.08 days/kg per month during the maintenance period.

In another embodiment, the invention provides a use of Cladribine according to the invention wherein the pharmaceutical formulation is to be orally administered at a daily dose of about 10 mg Cladribine from day 1 to about day 2 each month during the induction period.

In another embodiment, the invention provides a use of Cladribine according to the invention wherein the pharmaceutical formulation is to be orally administered at a daily dose of about 10 mg Cladribine from day 1 to about day 3 each month during the induction period.

In another embodiment, the invention provides a use of Cladribine according to the invention wherein the pharmaceutical formulation is to be orally administered at a daily dose of about 10 mg Cladribine from day 1 to about day 4 each month during the induction period.

In another embodiment, the invention provides a use of Cladribine according to the invention wherein the pharmaceutical formulation is to be orally administered at a daily dose of about 10 mg Cladribine from day 1 to about day 5 each month during the induction period.

In another embodiment, the invention provides a use of Cladribine according to the invention wherein the pharmaceutical formulation is to be orally administered at a daily dose of about 10 mg Cladribine from day 1 to about day 6 each month during the induction period.

In another embodiment, the invention provides a use of Cladribine according to the invention wherein the pharmaceutical formulation is to be orally administered at a daily dose of about 10 mg Cladribine from day 1 to about day 4 each month during the induction period and wherein the pharmaceutical formulation is a pharmaceutical formulation described in WO 2004/087101 or in WO 2004/087100.

In another embodiment, the invention provides a use of Cladribine according to any of the preceding claims wherein the pharmaceutical formulation is to be administered in combination with interferon-beta.

In a preferred embodiment, the invention provides a method for the treatment of multiple sclerosis, comprising the oral administration of Cladribine or of a pharmaceutical formulation thereof in a patient in need thereof comprising the following steps:
  (i) An induction period wherein Cladribine or a pharmaceutical formulation thereof is administered and wherein the total dose of Cladribine reached at the end of the induction period is from about 1.5 mg/kg to about 3.5 mg/kg;
  (ii) A Cladribine-free period wherein no Cladribine is administered;
  (iii) A maintenance period wherein Cladribine or a pharmaceutical formulation thereof is administered and wherein the total dose of Cladribine reached at the end of the maintenance period is lower than the total dose of Cladribine reached at the end of the induction period (i);
  (iv) A Cladribine-free period wherein no Cladribine is administered.

In a preferred embodiment, the invention provides a method for the treatment of multiple sclerosis, comprising the oral administration of Cladribine or of a pharmaceutical formulation thereof in a patient in need thereof comprising the following steps:
  (i) An induction period wherein Cladribine or a pharmaceutical formulation thereof is administered and wherein the total effective dose of Cladribine reached at the end of the induction period is from about 0.7 mg/kg to about 1.4 mg/kg;
  (ii) A Cladribine-free period wherein no Cladribine is administered;
  (iii) A maintenance period wherein Cladribine pharmaceutical formulation is administered and wherein the total effective dose of Cladribine reached at the end of the maintenance period is lower than the total effective dose of Cladribine reached at the end of the induction period (i);
  (iv) A Cladribine-free period wherein no Cladribine is administered.

In another further embodiment, the invention provides a method according to the invention wherein the steps (iii) to (iv) are repeated at least one or two times.

In a preferred embodiment, the invention provides a method of treating multiple sclerosis with Cladribine, wherein Cladribine is orally administered following the sequential steps below:
  (i) Administering Cladribine, such that the total dose of Cladribine reached at the end of the induction period is from about 1.7 mg/kg to about 3.5 mg/kg;
  (ii) Administering no Cladribine during a Cladribine free period;

(iii) Administering Cladribine such that the total dose of Cladribine reached at the end of a maintenance period is lower than the total dose of Cladribine reached at the end of the induction period (i);

(iv) And optionally, a Cladribine-free period wherein no Cladribine is administered.

In a further preferred embodiment, the invention provides a method wherein the induction period lasts up to about 4 months, or up to about 3 months, or up to about 2 months.

In a further preferred embodiment, the invention provides a method wherein the total dose of Cladribine reached at the end of the induction period is about 1.7 mg/kg.

In a further preferred embodiment, the invention provides a method wherein the total dose of Cladribine reached at the end of the induction period is about 3.5 mg/kg.

In a further preferred embodiment, the invention provides a method wherein the total effective dose of Cladribine reached at the end of the induction period is about 1.4 mg/kg.

In a further preferred embodiment, the invention provides a method wherein the Cladribine-free period lasts up to about 10 months, or up to about 9 months, or up to about 8 months.

In a further preferred embodiment, the invention provides a method wherein the maintenance period lasts up to about 4 months, or up to about 3 months or up to about 2 months.

In a further preferred embodiment, the invention provides a method wherein the total dose of Cladribine reached at the end of the maintenance period is about 1.7 mg/kg.

In a further preferred embodiment, the invention provides a method wherein the total effective dose of Cladribine reached at the end of the maintenance period is about 0.7 mg/kg.

In a further preferred embodiment, the invention provides a method wherein the maintenance period is followed by a Cladribine-free period.

In another further embodiment, the invention provides a method according to the invention wherein the total dose of Cladribine reached at the end of the induction period is about 3.5 mg/kg and the total dose of Cladribine reached at the end of the maintenance period is about 1.7 mg/kg.

In another further embodiment, the invention provides a method according to the invention wherein the total effective dose of Cladribine reached at the end of the induction period is about 1.4 mg/kg and the total effective dose of Cladribine reached at the end of the maintenance period is about 0.7 mg/kg.

In another further embodiment, the invention provides a method according to the invention wherein Cladribine is to be orally administered at a daily dose of about 3 to about 30 mg.

In another further embodiment, the invention provides a method according to the invention wherein Cladribine is to be orally administered at a daily dose of about 10 mg.

In another further embodiment, the invention provides a method according to the invention wherein Cladribine is orally administered about 1 to about 7 days per month during the induction period.

In another further embodiment, the invention provides a method according to the invention wherein the steps (iii) are repeated at least one or two times.

In another further embodiment, the invention provides a method according to the invention wherein Cladribine is to be administered in combination with interferon-beta.

EXAMPLES

The following abbreviations refer respectively to the definitions below:

kg (kilogram), μg (microgram), mg (milligram), AEs (Adverse effects), CNS (Cnetral nervous system), CSF (Cerebrospinal fluid), EDSS (Expanded Disability Status Scale, SNRS (Scripps Neurologic Rating Scale), IFN (interferon), i.v. (intra-veinous), MIU (Million International units), MS (multiple sclerosis), MRI (Magnetic resonance imaging), p.o. (per os), PPMS (Primary progressive multiple sclerosis), PRMS (Progressive relapsing multiple sclerosis), RRMS (Relapsing-remitting multiple sclerosis), SPMS (Secondary progressive multiple sclerosis), s.c. (subcutaneous), TIW (Three times a week), 2-CdA (2-chloro-2'deoxyadenosine or Cladribine), UI; (International unit).

The efficacy and safety of oral Cladribine administration, eventually multi-dose administration, according to the invention can be assessed for example following the protocol below:

Example 1

Oral Cladribine in the Treatment of Relapsing Forms of MS

A study of sixty patients with relapsing forms of clinically definite multiple sclerosis is undertaken. Each patient is first examined for normal hepatic, renal, and bone marrow functioning to establish baseline values.

Patients are selected from Male or Female, between 18 and 55 years of age who had one or more relapses within the prior 12 months. Female patients are non-pregnant female. Patients are randomly assigned to one of the treatment groups listed in Table 1 below:

TABLE 1

| Group | 2-CdA |
|---|---|
| 1 | — |
| 2 | 1.75 mg/kg |
| 3 | 3.5 mg/kg |

Each of the patients in Groups 2 and 3 receives 3 mg or 10 mg 2-CdA (1, 2 or 3 administration(s) a day depending on the patient's weight) combined in cyclodextrin formulation as described in WO 2004/087101, Example 3. The Compositions of the Cladribine formulations in 3 mg or 10 mg 2-CdA tablets containing hydroxypropyl-beta-cyclodextrin are listed in Table 2 below:

TABLE 2

| Name of ingredients | Formula mg/tablet | Formula mg/tablet |
|---|---|---|
| Cladribine-2-hydroxypropyl-β-cyclodextrin- complex* | 153.75 equivalent to 10 mg 2-CdA | 30.60 equivalent to 3 mg 2-CdA |
| Sorbitol powder | 44.25 | 68.4 |
| Magnesium Stearate (vegetable grade) | 2.0 | 1.00 |
| Total | 200.0 | 100 |

*Cladribine is complexed and lyophilised with 2-hydroxypropyl-β-cyclodextrin as a separate process as described in WO 2004/087101.

Examples of administration schemes for the induction period depending on the patient's weight are given below in Tables 3 and 4 for the target doses of 1.75 mg/kg and 3.5 mg/kg respectively. For the maintenance period, the example of administration scheme of Table 3 is applicable.

TABLE 3

| Patient weight ranges (kg) | | | Total target dose (kg) equivalent to 1.75 mg/kg | | Number of pills (10 mg)/induction period | | |
|---|---|---|---|---|---|---|---|
| Min | Mid range | Max | Min | Max | Month 1 | Month 2 | Total |
| 40 | 42.5 | 44.9 | 28 | 31.4 | 4 | 3 | 7 |
| 45 | 47.5 | 49.9 | 31.5 | 34.9 | 4 | 4 | 8 |
| 50 | 52.5 | 54.9 | 35 | 38.4 | 5 | 4 | 9 |
| 55 | 57.5 | 59.9 | 38.5 | 41.9 | 5 | 5 | 10 |
| 60 | 62.5 | 64.9 | 42 | 45.4 | 5 | 5 | 10 |
| 65 | 67.5 | 69.9 | 45.5 | 48.9 | 6 | 5 | 11 |
| 70 | 72.5 | 74.9 | 49 | 52.4 | 6 | 6 | 12 |
| 75 | 77.5 | 79.9 | 52.5 | 55.9 | 7 | 6 | 13 |
| 80 | 82.5 | 84.9 | 56 | 59.4 | 7 | 6 | 13 |
| 85 | 87.5 | 89.9 | 59.5 | 62.9 | 7 | 7 | 14 |
| 90 | 92.5 | 94.9 | 63 | 66.4 | 8 | 7 | 15 |
| 95 | 97.5 | 99.9 | 66.5 | 69.9 | 8 | 8 | 16 |
| 100 | 102.5 | 104.9 | 70 | 73.4 | 9 | 8 | 17 |
| 105 | 107.5 | 109.9 | 73.5 | 76.9 | 9 | 9 | 18 |
| 110 | 112.5 | 114.9 | 77 | 80.4 | 9 | 9 | 18 |
| 115 | 117.5 | 119.9 | 80.5 | 83.9 | 10 | 9 | 19 |

TABLE 4

| Patient weight ranges (kg) | | | Total target dose (kg) equivalent to 3.5 mg/kg | | Number of pills (10 mg)/induction period | | | | |
|---|---|---|---|---|---|---|---|---|---|
| Min | Mid range | Max | Min | Max | Month 1 | Month 2 | Month 3 | Month 4 | Total |
| 40 | 42.5 | 44.9 | 56 | 62.9 | 4 | 4 | 3 | 3 | 14 |
| 45 | 47.5 | 49.9 | 63 | 69.9 | 4 | 4 | 4 | 4 | 16 |
| 50 | 52.5 | 54.9 | 70 | 76.9 | 5 | 4 | 4 | 4 | 17 |
| 55 | 57.5 | 59.9 | 77 | 83.9 | 5 | 5 | 5 | 4 | 19 |
| 60 | 62.5 | 64.9 | 84 | 90.9 | 6 | 5 | 5 | 5 | 21 |
| 65 | 67.5 | 69.9 | 91 | 97.9 | 6 | 6 | 5 | 5 | 22 |
| 70 | 72.5 | 74.9 | 98 | 104.9 | 6 | 6 | 6 | 6 | 24 |
| 75 | 77.5 | 79.9 | 105 | 111.9 | 7 | 7 | 6 | 6 | 26 |
| 80 | 82.5 | 84.9 | 112 | 118.9 | 7 | 7 | 7 | 6 | 27 |
| 85 | 87.5 | 89.9 | 119 | 125.9 | 7 | 7 | 7 | 7 | 28 |
| 90 | 92.5 | 94.9 | 126 | 132.9 | 8 | 8 | 7 | 7 | 30 |
| 95 | 97.5 | 99.9 | 133 | 139.9 | 8 | 8 | 8 | 8 | 32 |
| 100 | 102.5 | 104.9 | 140 | 146.9 | 9 | 8 | 8 | 8 | 33 |
| 105 | 107.5 | 109.9 | 147 | 153.9 | 9 | 9 | 9 | 8 | 35 |
| 110 | 112.5 | 114.9 | 154 | 160.9 | 10 | 9 | 9 | 9 | 37 |
| 115 | 117.5 | 119.9 | 161 | 167.9 | 10 | 10 | 9 | 9 | 38 |

In Group 1 patients receive a placebo (saline) for 4 months followed by 8 months of no treatment.

In Group 2 patients receive a daily oral administration of Cladribine for about 5 days a month during 2 months (induction period) of 2-CdA cyclodextrin formulation such as the total effective dose administered at the end of the first 2 months approximates about 0.7 mg/kg (total dose of about 1.75 mg/kg for a bioavailability of about 40%); followed by administration of placebo for 2 months; followed by 8 months of no treatment.

In Group 3 patients receive a daily oral administration of Cladribine for about 5 days a month during 4 months (induction period) of 2-CdA cyclodextrin formulation such as the total effective dose administered at the end of the first 4 months approximates about 1.4 mg/kg (total dose of about 3.5 mg/kg for a bioavailability of about 40%); followed by 8 months of no treatment.

Beginning at month 13, all 3 patient groups receive re-treatment with Cladribine cyclodextrin formulation for about 5 days a month for 2 months (maintenance period) with the lower dose (such as the total effective dose administered at the end of the first 2 months approximates about 0.7 mg/kg) followed by 10 months of no treatment.

Finally, beginning at month 25, all patient groups receive re-treatment with Cladribine cyclodextrin formulation for about 5 days a month for 2 months (maintenance period) with the lower dose (such as the total effective dose administered at the end of the first 2 months approximates about 0.7 mg/kg) followed by 10 more months of no treatment.

Patients are monitored to determine whether there is any progression or improvement of brain lesions associated with progression of MS through MRI scans and neurological examination as described in Miller et al., 1996, above; Evans et al., 1997, above; Sipe et al., 1984, above; and Mattson, 2002, above. All patients have a baseline and MRI study (brain or spinal cord, according to localization of the lesions) at month 12.

The patient's disability progression and the time for having a first relapse are monitored as well as the proportion of relapse-fee patients at 24 months.

Lymphocyte markers and monocyte counts are monitored in the patients.

Patients in Groups 2 and 3 have a decrease in brain lesions.

The data show that the 2-CdA regimen consisting in the succession of an induction treatment and maintenance treatments is efficient in decreasing brain lesions and no severe adverse effect is observed.

The invention claimed is:

1. A method of treating multiple sclerosis comprising the oral administration of a formulation comprising cladribine, wherein the formulation is to be orally administered following the sequential steps below:
   (i) an induction period wherein said cladribine formulation is administered and wherein the total dose of cladribine reached at the end of the induction period is from about 1.7 mg/kg to about 3.5 mg/kg;
   (ii) a cladribine-free period of between about 8 and about 10 months wherein no cladribine formulation is administered;
   (iii) a maintenance period wherein said cladribine formulation is administered and wherein the total dose of cladribine reached at the end of the maintenance period is lower than the total dose of cladribine reached at the end of the induction period (i); and (iv) a cladribine-free period wherein no cladribine formulation is administered.

2. The method according to claim 1, wherein the induction period lasts up to about 4 months.

3. The method according to claim 2, wherein the induction period lasts about 2 months.

4. The method according to claim 2, wherein the induction period lasts about 3 months.

5. The method according to claim 2, wherein the induction period lasts about 4 months.

6. The method according to claim 2, wherein the induction period lasts up to about 3 months.

7. The method according to claim 1, wherein the total dose of cladribine reached at the end of the induction period is about 1.7 mg/kg.

8. The method according to claim 1, wherein the total dose of cladribine reached at the end of the induction period is about 3.5 mg/kg.

9. The method according to claim 1, wherein the cladribine-free (iv) period lasts about 10 months.

10. The method according to claim 1, wherein the maintenance period lasts about 4 months.

11. The method according to claim 1, wherein the total dose of cladribine reached at the end of the maintenance period is about 1.7 mg/kg.

12. The method according to claim 1, wherein the formulation is to be orally administered following the sequential steps below:

(i) an induction period wherein said cladribine formulation is orally administered and wherein the total dose of cladribine reached at the end of the induction period is from about 1.7 mg/kg to about 3.5 mg/kg;

(ii) a cladribine-free period of between about 8 and about 10 months wherein no cladribine formulation is administered;

(iii) a maintenance period wherein said cladribine formulation is administered and wherein the total dose of cladribine reached at the end of the maintenance period is lower than the total dose of cladribine reached at the end of the induction period (i); and (iv) a cladribine-free period wherein no cladribine formulation is administered;

wherein the induction period lasts up to 4 months; the cladribine-free period (ii) lasts up to 10 months; the maintenance period (iii) lasts up to 2 months; the cladribine-free period (iv) lasts up to 10 months; the total dose of cladribine reached at the end of the maintenance period is about 1.7 mg/kg and steps (iii) to (iv) are repeated one, two or three times.

13. The method according to claim 12, wherein the total dose of cladribine reached at the end of the induction period is about 3.5 mg/kg and the total dose of cladribine reached at the end of the maintenance period is about 1.7 mg/kg.

14. The method according to claim 12, wherein the formulation is to be orally administered at a daily dose of 3 to 30 mg cladribine.

15. The method according to claim 14, wherein the formulation is to be orally administered at a daily dose of 10 mg cladribine.

16. The method according to claim 1, wherein the formulation is orally administered 1 to 7 days per month during the induction period.

17. The method according to claim 1, wherein the steps (iii) to (iv) are repeated at least one or two times.

18. The method according to claim 1, wherein said cladribine formulation is to be administered in combination with interferon-beta.

19. The method according to claim 12, wherein said cladribine formulation is to be administered in combination with interferon-beta.

20. A method of treating multiple sclerosis comprising the oral administration of a formulation comprising cladribine following the sequential steps below:

(i) an induction period lasting from about 2 months to about 4 months wherein said formulation is orally administered and wherein the total dose of cladribine reached at the end of the induction period is from about 1.7 mg/kg to about 3.5 mg/kg;

(ii) a cladribine-free period lasting from about 8 months to about 10 months, wherein no cladribine is administered;

(iii) a maintenance period lasting from about 2 months to about 4 months, wherein said formulation is orally administered and wherein the total dose of cladribine reached at the end of the maintenance period is lower than the total dose of cladribine reached at the end of the induction period (i);

(iv) a cladribine-free period wherein no cladribine is administered.

21. The method according to claim 20, wherein the induction period lasts about 4 months.

22. The method according to claim 20, wherein the induction period lasts about 2 months.

23. The method according to claim 20, wherein the total dose of cladribine reached at the end of the induction period is about 1.7 mg/kg.

24. The method according to claim 20, where the total dose of cladribine reached at the end of the induction period is about 3.5 mg/kg.

25. The method according to claim 20, wherein the cladribine-free period (ii) lasts about 10 months.

26. The method according to claim 20, wherein the cladribine-free (iv) period lasts 10 months.

27. The method according to claim 20, wherein the maintenance period lasts about 2 months.

28. The method according to claim 20, wherein the formulation is orally administered following the sequential steps below:

(i) an induction period wherein said formulation is administered orally and wherein the total dose of cladribine reached at the end of the induction period is from about 1.7 mg/kg to about 3.5 mg/kg;

(ii) a cladribine-free period wherein no cladribine is administered;

(iii) a maintenance period wherein said formulation is administered orally and wherein the total dose of cladribine reached at the end of the maintenance period is lower than the total dose of cladribine reached at the end of the induction period (i); (iv) a cladribine-free period wherein no cladribine is administered;

wherein the maintenance period (iii) lasts about 2 months; the cladribine-free period (iv) lasts about 10 months; the total dose of cladribine reached at the end of the maintenance period is about 1.7 mg/kg and steps (iii) to (iv) are repeatedly performed one, two or three times.

29. The method according to claim 20, wherein the total dose of cladribine reached at the end of the induction period is about 3.5 mg/kg and the total dose of cladribine reached at the end of the maintenance period is about 1.7 mg/kg.

30. The method according to claim 20, wherein the formulation is orally administered at a daily dose of 3 to 30 mg cladribine.

31. The method according to claim 20, wherein the formulation is orally administered at a daily dose of 10 mg cladribine.

32. The method according to claim 20, wherein the formulation is orally administered 1 to 7 days per month during the induction period.

33. The method according to claim 20, wherein the steps (iii) to (iv) are repeated at least one time.

34. The method according to claim 20, wherein the steps (iii) to (iv) are repeated at least two times.

35. The method according to claim 20, wherein the formulation is administered in combination with interferon-beta.

36. A method of treating multiple sclerosis comprising the oral administration of a formulation comprising cladribine following the sequential steps below:
   (i) an induction period lasting from about 2 months to about 4 months wherein said formulation is orally administered and wherein the total dose of cladribine reached at the end of the induction period is from about 1.7 mg/kg to about 3.5 mg/kg;
   (ii) a cladribine-free period lasting from about 8 months to about 10 months, wherein no cladribine is administered;
   (iii) a maintenance period lasting from about 2 months to about 4 months, wherein said formulation is orally administered and wherein the total dose of cladribine reached at the end of the maintenance period is about 1.7 mg/kg;
   (iv) a cladribine-free period wherein no cladribine is administered.

37. The method according to claim 36, wherein the induction period lasts about 4 months.

38. The method according to claim 36, wherein the induction period lasts about 2 months.

39. The method according to claim 36, wherein the total dose of cladribine reached at the end of the induction period is about 1.7 mg/kg.

40. The method according to claim 36, where the total dose of cladribine reached at the end of the induction period is about 3.5 mg/kg.

41. The method according to claim 36, wherein the cladribine-free period (ii) lasts about 10 months.

42. The method according to claim 36, wherein the cladribine-free (iv) period lasts 10 months.

43. The method according to claim 36, wherein the maintenance period lasts about 2 months.

44. The method according to claim 36, wherein the formulation is orally administered at a daily dose of 3 to 30 mg cladribine.

45. The method according to claim 36, wherein the formulation is orally administered at a daily dose of 10 mg cladribine.

46. The method according to claim 36, wherein the formulation is orally administered 1 to 7 days per month during the induction period.

47. The method according to claim 36, wherein the steps (iii) to (iv) are repeated at least one or two times.

48. The method according to claim 36, wherein the formulation is administered in combination with interferon-beta.

* * * * *

UNITED STATES PATENT AND TRADEMARK OFFICE
CERTIFICATE OF CORRECTION

PATENT NO. : 7,713,947 B2
APPLICATION NO. : 11/722018
DATED : May 11, 2010
INVENTOR(S) : Giampiero De Luca et al.

It is certified that error appears in the above-identified patent and that said Letters Patent is hereby corrected as shown below:

Column 1,
Line 31, "Clinical is disability" should read --Clinical disability--.

Column 7,
Line 32, "WFN-beta, WFN-beta" should read --IFN-beta, IFN-beta--.

Column 14,
Line 12, "UI; (International unit)" should read --UI (International unit)--.

Signed and Sealed this

Fifteenth Day of June, 2010

David J. Kappos
*Director of the United States Patent and Trademark Office*